US008562680B2

(12) United States Patent
Hays et al.

(10) Patent No.: US 8,562,680 B2
(45) Date of Patent: *Oct. 22, 2013

(54) GRAFT LIGAMENT ANCHOR AND METHOD FOR ATTACHING A GRAFT LIGAMENT TO A BONE

(76) Inventors: Jo Hays, Logan, UT (US); David Overaker, Annandale, NJ (US); Joseph Contiliano, Stewartsville, NJ (US); Joseph H. Sklar, Longmeadow, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/253,190

(22) Filed: Oct. 5, 2011

(65) Prior Publication Data

US 2012/0053691 A1     Mar. 1, 2012

Related U.S. Application Data

(63) Continuation of application No. 11/781,369, filed on Jul. 23, 2007, now Pat. No. 8,048,158, which is a continuation of application No. 10/387,674, filed on Mar. 13, 2003, now Pat. No. 7,329,281, which is a continuation of application No. 09/966,766, filed on Sep. 28, 2001, now Pat. No. 6,554,862, which is a continuation-in-part of application No. 09/789,398, filed on Feb. 20, 2001, now abandoned, which is a continuation of application No. 09/304,885, filed on May 4, 1999, now abandoned, which is a continuation of application No. 08/756,413, filed on Nov. 27, 1996, now Pat. No. 5,899,938.

(51) Int. Cl.
    *A61F 2/08*     (2006.01)
(52) U.S. Cl.
    USPC ....... 623/13.14; 623/13.15; 606/60; 606/151; 606/232

(58) Field of Classification Search
    USPC ............. 623/13.11–13.2; 606/60, 151, 232
    See application file for complete search history.

(56) References Cited

U.S. PATENT DOCUMENTS

| RE13,204 E | 2/1911 | Jossart |
| 2,353,851 A | 7/1944 | Rosan |
| 3,153,975 A | 10/1964 | Rapata |
| 3,199,398 A | 8/1965 | Weisz |
| 3,411,397 A | 11/1968 | Birmingham |

(Continued)

FOREIGN PATENT DOCUMENTS

| CA | 1015989 | 8/1977 |
| DE | 1015989 | 9/1957 |

(Continued)

OTHER PUBLICATIONS

European Search Report, from 11156055.3, dated Apr. 15, 2011.

(Continued)

*Primary Examiner* — David H Willse
*Assistant Examiner* — Javier Blanco

(57) ABSTRACT

A graft ligament anchor comprises a graft ligament engagement member disposed in an opening in a bone, the graft ligament engagement member being arranged to receive a graft ligament alongside the engagement member, and a locking member for disposition in the opening, and at least in part engageable with the graft ligament engagement member. Movement of the locking member in the opening causes the locking member to urge the engagement member, and the graft ligament therewith, toward a wall of the opening, to secure the graft ligament to the wall of the opening. A method for attaching a graft ligament to a bone is also provided.

12 Claims, 20 Drawing Sheets

(56) References Cited

U.S. PATENT DOCUMENTS

| | | |
|---|---|---|
| 3,516,324 A | 6/1970 | Berner |
| 3,678,798 A | 7/1972 | Van Niel |
| 3,731,724 A | 5/1973 | Dorfinger |
| 3,765,295 A | 10/1973 | Ptak |
| 3,832,931 A | 9/1974 | Talan et al. |
| 3,942,407 A | 3/1976 | Mortensen |
| 3,976,079 A | 8/1976 | Samuels et al. |
| 4,083,289 A | 4/1978 | Erickson |
| 4,085,651 A | 4/1978 | Koscik |
| 4,407,618 A | 10/1983 | Kimura |
| 4,484,570 A | 11/1984 | Sutter |
| 4,535,925 A | 8/1985 | Ramey et al. |
| 4,580,936 A | 4/1986 | Francis et al. |
| 4,590,928 A | 5/1986 | Hunt et al. |
| 4,708,132 A | 11/1987 | Silvestrini |
| 4,708,397 A | 11/1987 | Weinmann |
| 4,716,893 A | 1/1988 | Fischer et al. |
| 4,744,793 A | 5/1988 | Parr et al. |
| 4,755,183 A | 7/1988 | Kenna |
| 4,778,468 A | 10/1988 | Hunt et al. |
| 4,784,126 A | 11/1988 | Hourahane |
| 4,828,562 A | 5/1989 | Kenna |
| 4,851,005 A | 7/1989 | Hunt |
| 4,870,957 A | 10/1989 | Goble |
| 4,927,421 A | 5/1990 | Goble et al. |
| 4,940,467 A | 7/1990 | Tronzo |
| 4,944,742 A | 7/1990 | Clemow et al. |
| 4,950,270 A | 8/1990 | Bowman et al. |
| 4,950,271 A | 8/1990 | Lewis |
| 5,013,316 A | 5/1991 | Goble et al. |
| 5,037,422 A | 8/1991 | Hayhurst et al. |
| 5,062,843 A | 11/1991 | Mahony, III |
| 5,108,431 A | 4/1992 | Mansat |
| 5,147,362 A | 9/1992 | Goble |
| 5,151,104 A | 9/1992 | Kenna |
| 5,152,790 A | 10/1992 | Rosenbeg |
| 5,211,647 A | 5/1993 | Schmieding |
| 5,234,430 A | 8/1993 | Huebner |
| 5,236,445 A | 8/1993 | Hayhurst et al. |
| 5,268,001 A | 12/1993 | Nicholson et al. |
| 5,282,802 A | 2/1994 | Mahony, III |
| 5,312,438 A | 5/1994 | Johnson |
| 5,314,427 A | 5/1994 | Goble |
| 5,324,308 A | 6/1994 | Pierce |
| 5,356,435 A | 10/1994 | Thein |
| 5,360,448 A | 11/1994 | Thramann |
| 5,360,450 A | 11/1994 | Giannini |
| 5,376,119 A | 12/1994 | Zimmermann |
| 5,383,878 A | 1/1995 | Roger et al. |
| 5,425,707 A | 6/1995 | Goldberg |
| 5,425,767 A | 6/1995 | Steininger |
| 5,454,811 A | 10/1995 | Huebner |
| 5,458,601 A | 10/1995 | Young |
| 5,464,427 A | 11/1995 | Curtis et al. |
| 5,470,334 A | 11/1995 | Ross |
| 5,480,403 A | 1/1996 | Lee et al. |
| 5,486,197 A | 1/1996 | Le et al. |
| 5,489,210 A | 2/1996 | Hanosh |
| 5,562,669 A | 10/1996 | McGuire |
| 5,584,835 A | 12/1996 | Greenfield |
| 5,618,314 A | 4/1997 | Jamiolkowski et al. |
| 5,632,748 A | 5/1997 | Beck, Jr. et al. |
| 5,645,589 A | 7/1997 | Li |
| 5,702,397 A | 12/1997 | Goble et al. |
| 5,707,395 A | 1/1998 | Li |
| 5,725,529 A | 3/1998 | Nicholson et al. |
| 5,776,196 A | 7/1998 | Matsusaki |
| 5,895,425 A | 4/1999 | Grafton et al. |
| 5,899,938 A | 5/1999 | Sklar et al. |
| 5,906,632 A | 5/1999 | Bolton |
| 5,918,604 A | 7/1999 | Whelan |
| 5,948,001 A | 9/1999 | Larsen |
| 5,961,520 A | 10/1999 | Beck et al. |
| 5,989,253 A | 11/1999 | Bigliardi |
| 6,099,530 A | 8/2000 | Simonian et al. |
| 6,132,433 A | 10/2000 | Whelan |
| 6,283,973 B1 | 9/2001 | Hubbard |
| 6,355,066 B1 | 3/2002 | Kim |
| 6,371,124 B1 | 4/2002 | Whelan |
| 6,379,361 B1 | 4/2002 | Beck et al. |
| 6,387,129 B2 | 5/2002 | Rieser |
| 6,517,579 B1 | 2/2003 | Paulos et al. |
| 6,533,816 B2 | 3/2003 | Sklar |
| 6,537,319 B2 | 3/2003 | Whelan |
| 6,554,862 B2 | 4/2003 | Hays et al. |
| 6,558,094 B2 | 5/2003 | Nehl |
| 6,562,071 B2 | 5/2003 | Jarvinen |
| 6,575,987 B2 | 6/2003 | Gellman et al. |
| 6,589,245 B1 | 7/2003 | Weiler et al. |
| 6,616,694 B1 | 9/2003 | Hart |
| 6,623,524 B2 | 9/2003 | Schmieding |
| 6,632,245 B2 | 10/2003 | Kim |
| 6,673,094 B1 | 1/2004 | McDevitt et al. |
| 6,733,529 B2 | 5/2004 | Whelan |
| 6,746,483 B1 | 6/2004 | Bojarski et al. |
| 6,887,271 B2 | 5/2005 | Justin et al. |
| 6,932,841 B2 | 8/2005 | Sklar et al. |
| 6,939,379 B2 | 9/2005 | Sklar |
| 7,008,451 B2 | 3/2006 | Justin et al. |
| 7,083,647 B1 | 8/2006 | Sklar et al. |
| 7,261,716 B2 | 8/2007 | Strobel et al. |
| 7,309,355 B2 | 12/2007 | Donnelly et al. |
| 7,329,281 B2 | 2/2008 | Hays |
| 7,578,844 B2 | 8/2009 | Sklar |
| 7,637,949 B2 | 12/2009 | Hart |
| 7,901,456 B2 | 3/2011 | Justin |
| 8,048,158 B2 | 11/2011 | Hays et al. |
| 8,226,714 B2 | 7/2012 | Beck, Jr. et al. |
| 2001/0007074 A1 | 7/2001 | Strobel et al. |
| 2001/0047206 A1 | 11/2001 | Sklar et al. |
| 2002/0007182 A1 | 1/2002 | Kim |
| 2002/0040241 A1 | 4/2002 | Jarvinen |
| 2002/0055780 A1 | 5/2002 | Sklar |
| 2002/0072797 A1 | 6/2002 | Hays et al. |
| 2003/0065390 A1 | 4/2003 | Justin et al. |
| 2003/0135274 A1 | 7/2003 | Hays et al. |
| 2003/0144735 A1 | 7/2003 | Sklar et al. |
| 2003/0191530 A1 | 10/2003 | Sklar |
| 2004/0059415 A1 | 3/2004 | Schmieding |
| 2004/0068262 A1 | 4/2004 | Lemos et al. |
| 2004/0194789 A1 | 10/2004 | Whelan |
| 2004/0267361 A1 | 12/2004 | Donnelly et al. |
| 2005/0159748 A1 | 7/2005 | Clark |
| 2005/0171603 A1 | 8/2005 | Justin et al. |
| 2005/0216012 A1 | 9/2005 | Willimen |
| 2006/0052787 A1 | 3/2006 | Re et al. |
| 2006/0095130 A1 | 5/2006 | Caborn et al. |
| 2006/0095131 A1 | 5/2006 | Justin |
| 2006/0100627 A1 | 5/2006 | Stone et al. |
| 2006/0149258 A1 | 7/2006 | Sousa |
| 2006/0189991 A1 | 8/2006 | Bickley |
| 2007/0005069 A1 | 1/2007 | Contiliano et al. |
| 2007/0023259 A1 | 2/2007 | Schonauer |
| 2008/0015710 A1 | 1/2008 | Hays et al. |
| 2008/0133007 A1 | 6/2008 | Donnelly et al. |
| 2008/0154314 A1 | 6/2008 | McDevitt |
| 2008/0161806 A1 | 7/2008 | Donnelly et al. |
| 2008/0161864 A1 | 7/2008 | Beck et al. |
| 2008/0228271 A1 | 9/2008 | Stone et al. |
| 2010/0121449 A1 | 5/2010 | Sklar et al. |
| 2011/0112641 A1 | 5/2011 | Justin et al. |
| 2012/0053691 A1 | 3/2012 | Hays et al. |

FOREIGN PATENT DOCUMENTS

| | | |
|---|---|---|
| DE | 8901338 | 3/1989 |
| DE | 8914308 | 3/1990 |
| DE | 9109381 | 9/1991 |
| DE | 4127550 | 2/1993 |
| EP | 0358372 | 3/1990 |
| EP | 0425140 | 5/1991 |
| EP | 0596177 | 5/1994 |
| EP | 0596829 | 5/1994 |
| EP | 611557 | 8/1994 |

(56) References Cited

FOREIGN PATENT DOCUMENTS

| | | |
|---|---|---|
| EP | 0651979 | 5/1995 |
| EP | 0834281 | 4/1998 |
| EP | 1491162 | 12/2004 |
| FR | 2590792 | 6/1987 |
| FR | 2636835 | 3/1990 |
| FR | 2725615 | 4/1996 |
| JP | 5-300917 | 11/1993 |
| JP | 06-086783 A | 3/1994 |
| JP | 06-169944 A | 6/1994 |
| JP | 8066410 | 3/1996 |
| JP | 11-511357 A | 10/1999 |
| WO | WO 9428799 | 12/1994 |
| WO | WO 9822047 | 5/1998 |
| WO | WO 9823229 | 6/1998 |
| WO | WO 9952472 | 10/1999 |
| WO | WO 0106909 | 2/2001 |
| WO | WO 0130253 | 5/2001 |
| WO | WO 0195835 | 12/2001 |
| WO | WO 0232345 | 4/2002 |

OTHER PUBLICATIONS

Sklar, "Intrafix.TM. Technique for Tibial Fixation of ACL Grafts" Innovasive Devices, a company brochure of Mitek Products, Ethicon 1999—U.S. Appl. No. 09/304,885, Sklar et al., Filed May 4, 1999.
Japanese Office Action issued May 15, 2012 for Application No. 2007-254092 (8 Pages).

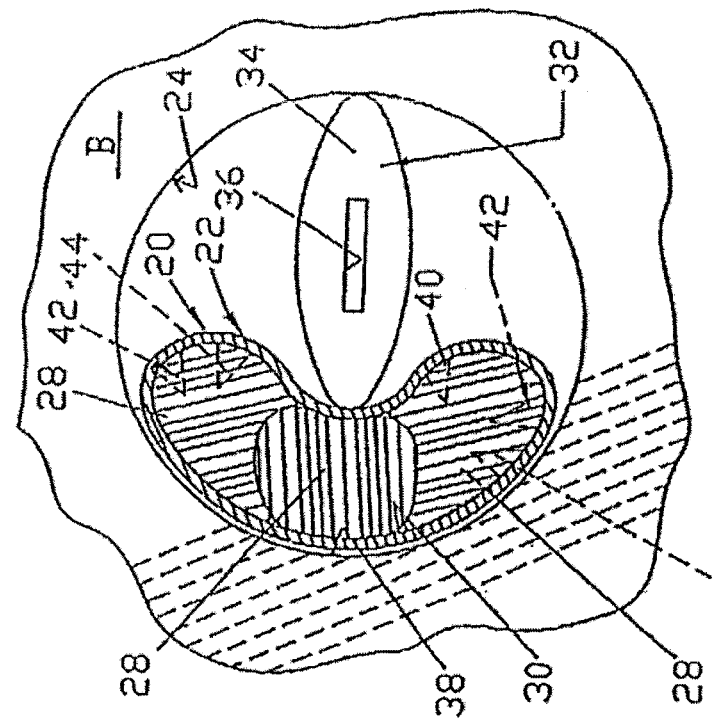
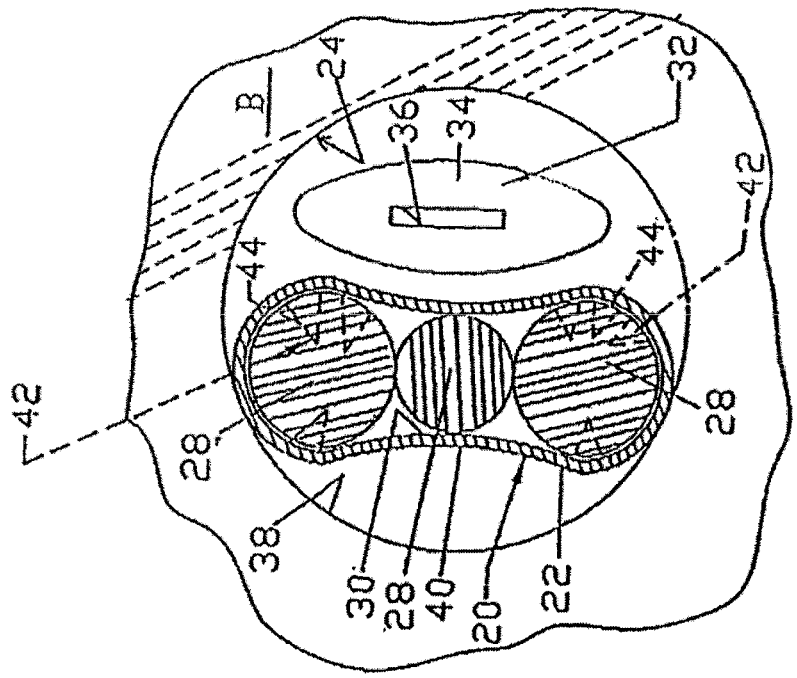

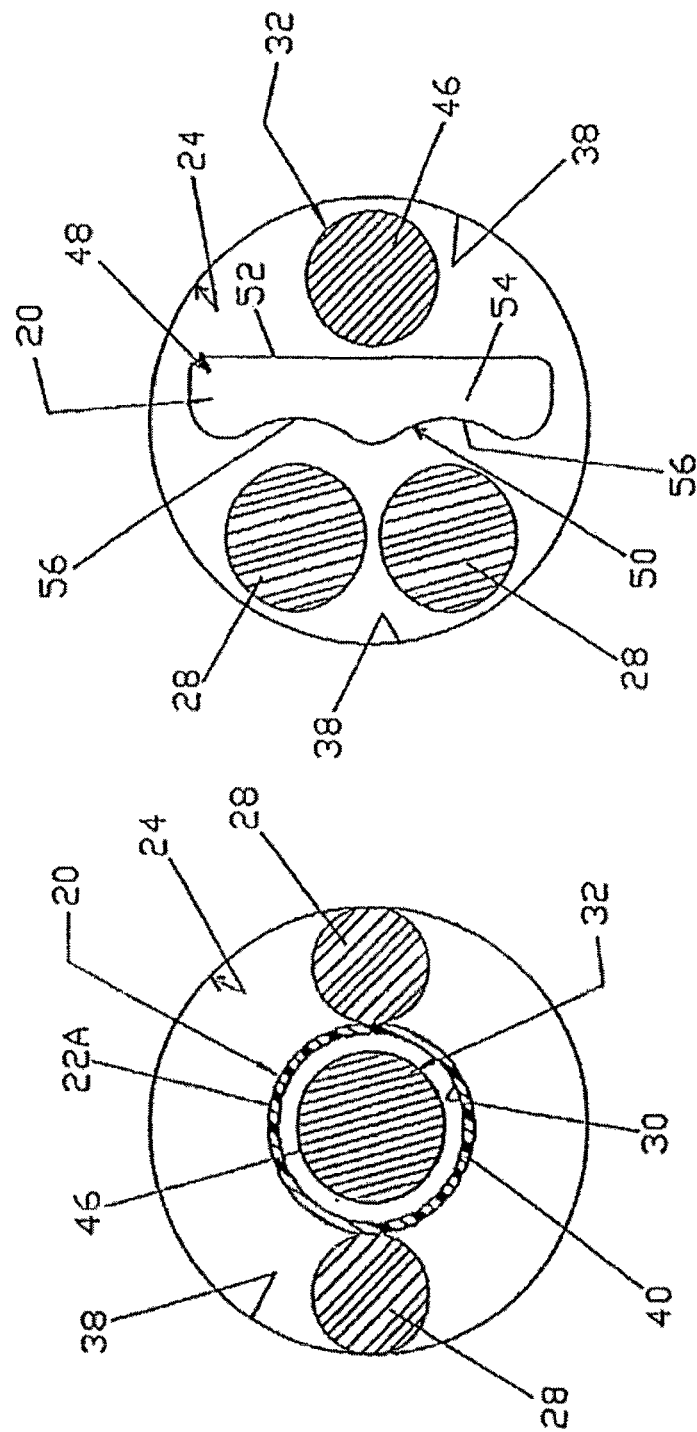

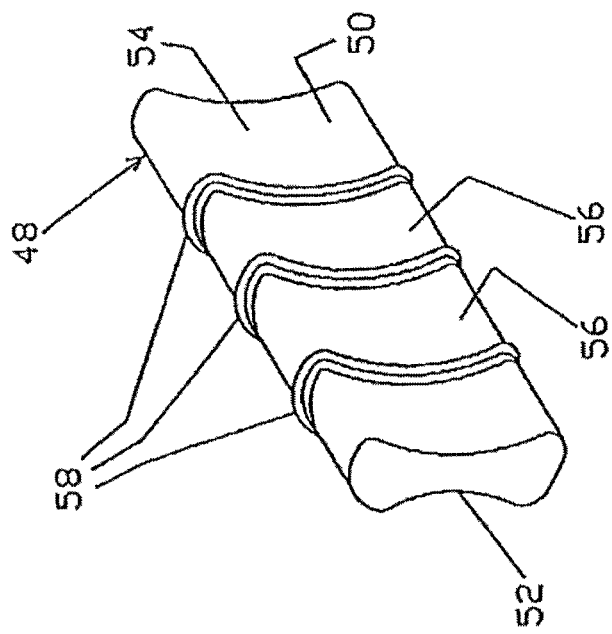
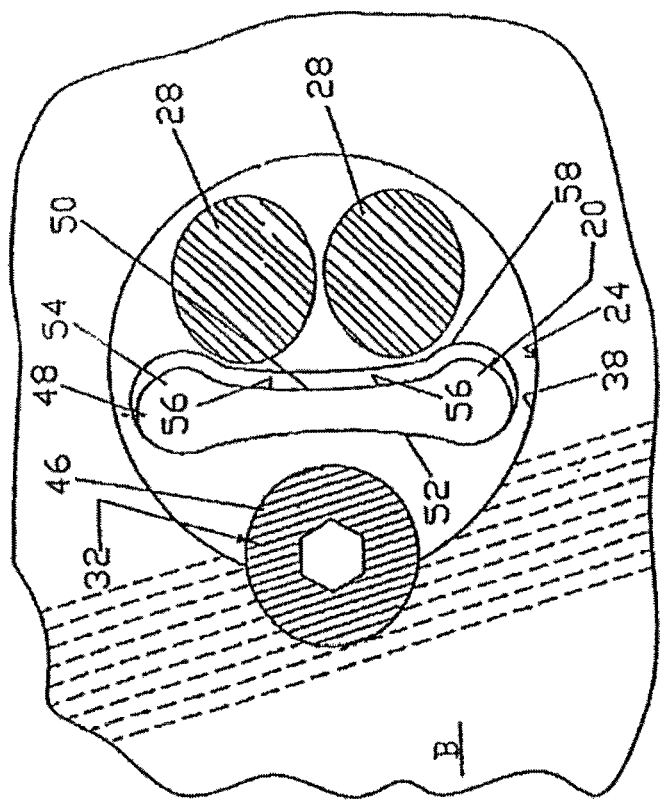

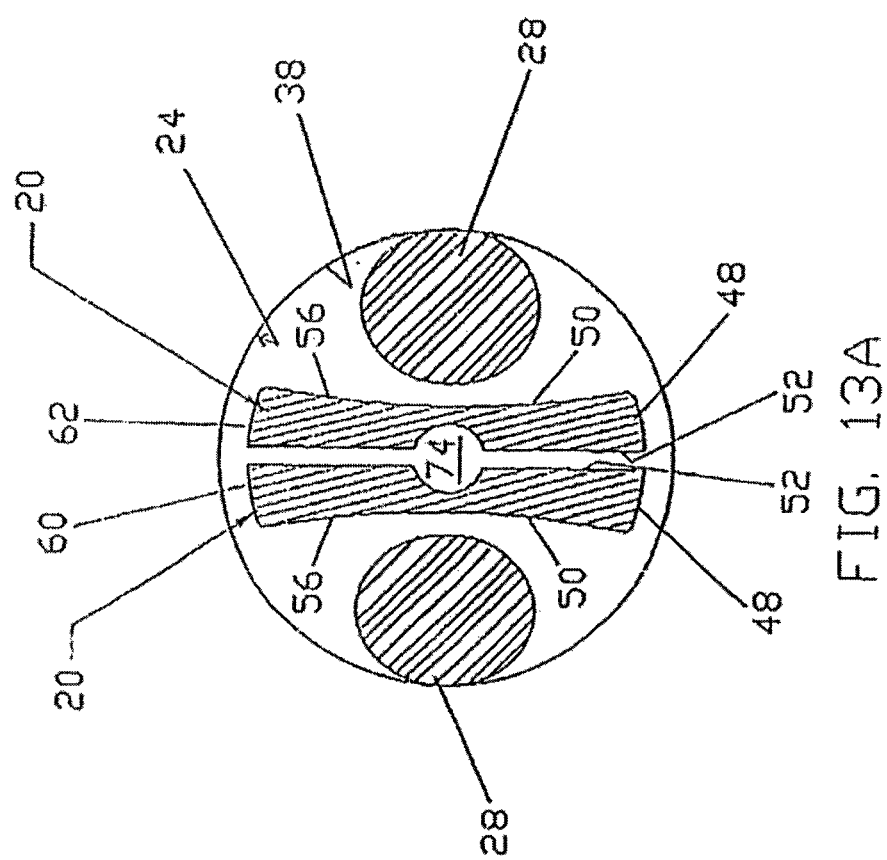

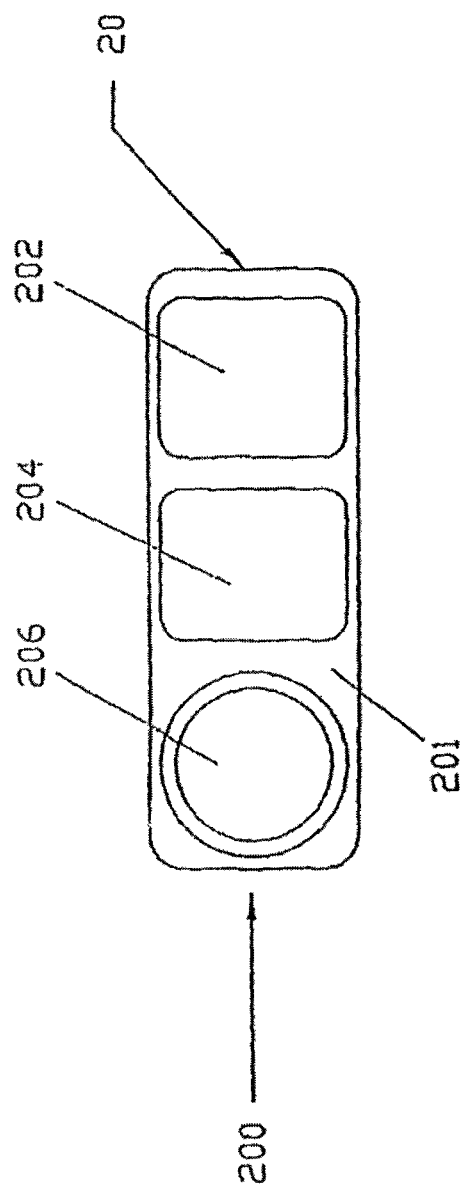
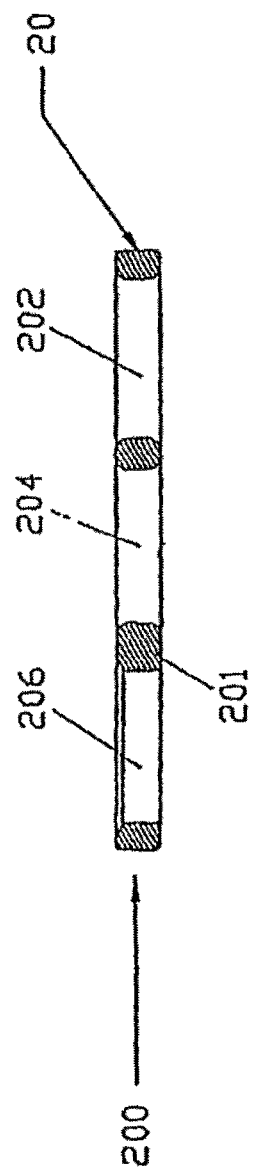

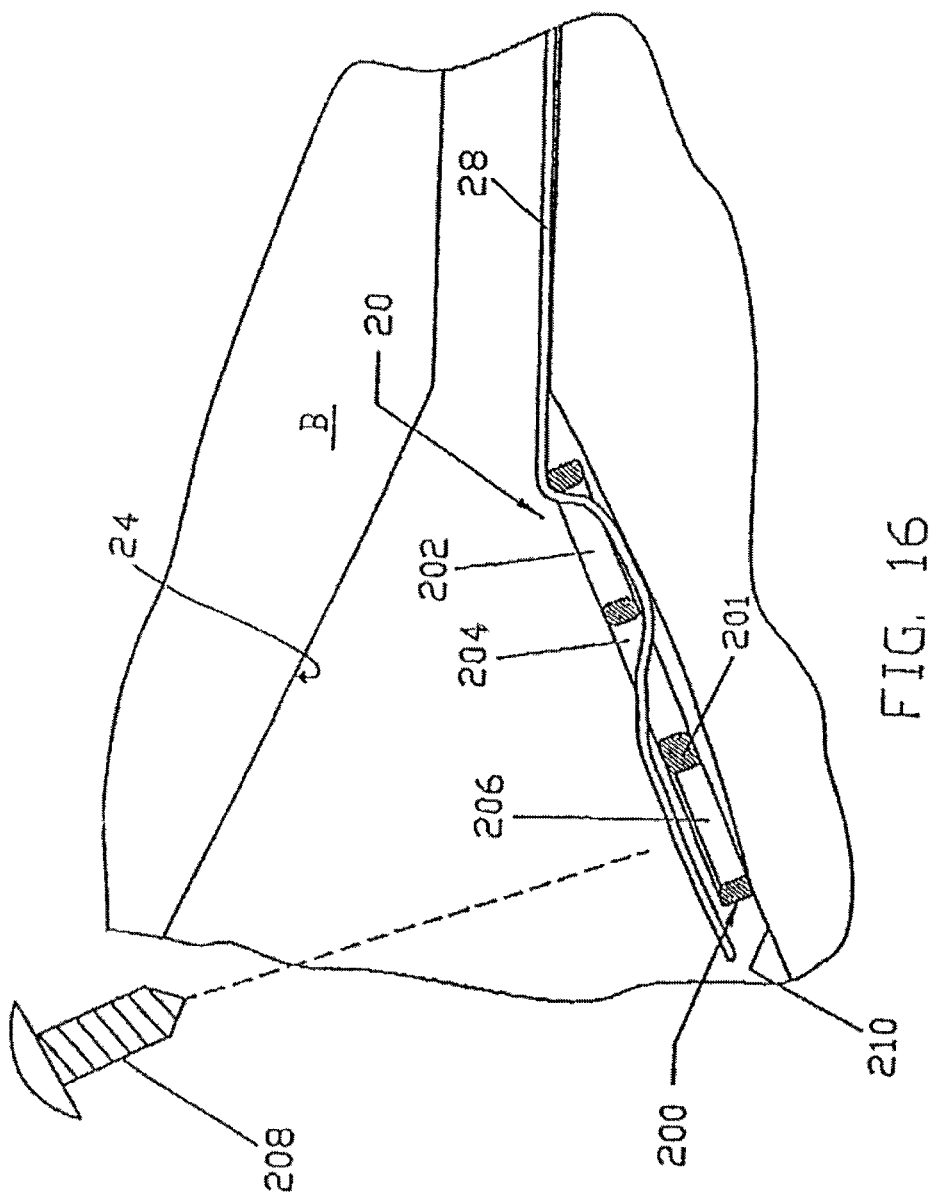

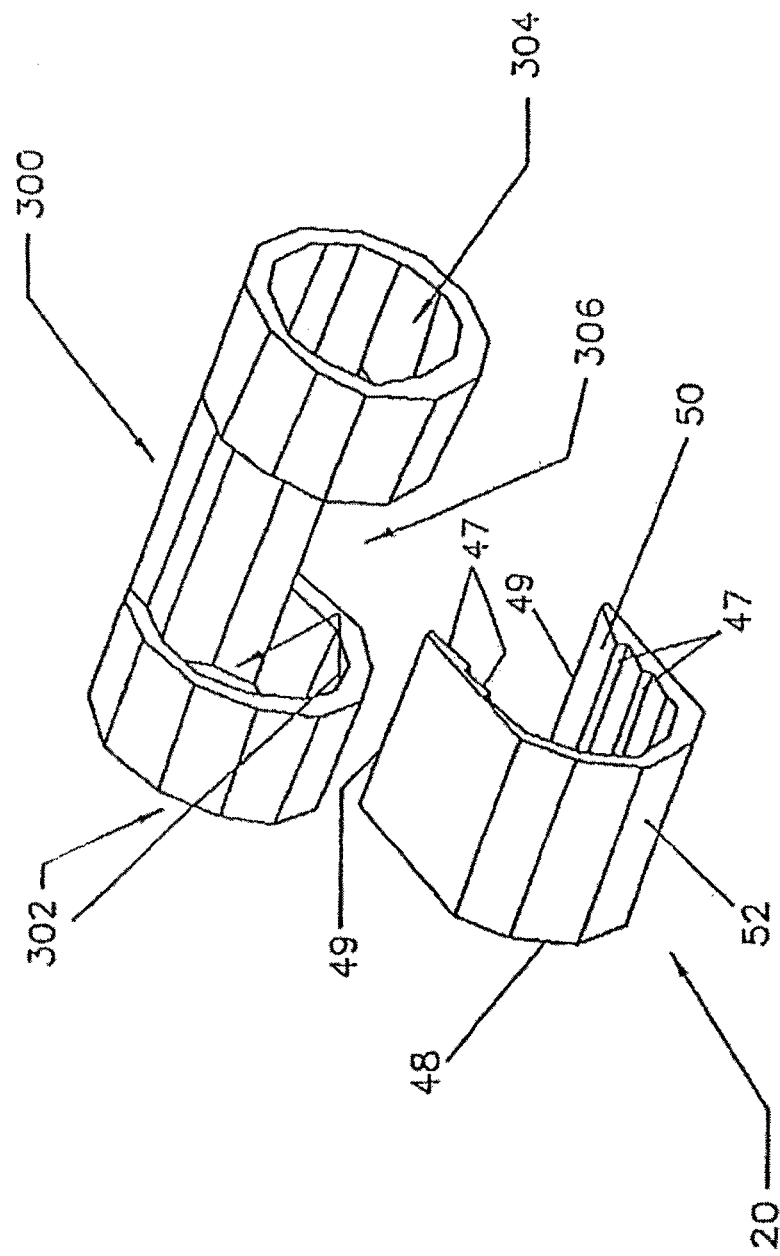

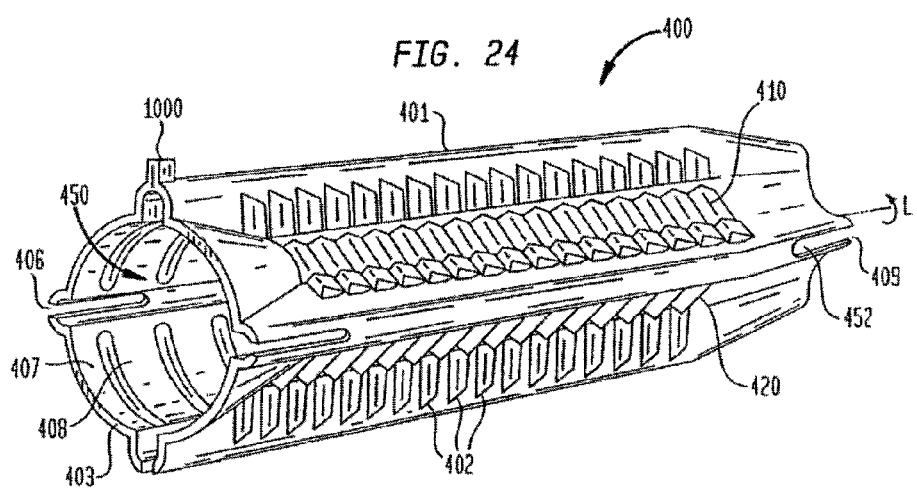

GRAFT LIGAMENT ANCHOR AND METHOD FOR ATTACHING A GRAFT LIGAMENT TO A BONE

RELATED APPLICATIONS

This application is a continuation of U.S. patent application Ser. No. 11/781,369, filed Jul. 23, 2007, now issued as U.S. Pat. No. 8,048,158 B2, which is a continuation of U.S. patent application Ser. No. 10/387,674, filed Mar. 13, 2003, now issued as U.S. Pat. No. 7,329,281, which is a continuation of U.S. patent application Ser. No. 09/966,766, filed Sep. 28, 2001, now issued as U.S. Pat. No. 6,554,862, which is a continuation-in-part of U.S. patent application Ser. No. 09/789,398, filed Feb. 20, 2001, now abandoned, which is a continuation of U.S. patent application Ser. No. 09/304,885, filed May 4, 1999, now abandoned, which is a continuation of Ser. No. 08/756,413, filed Nov. 27, 1996, now issued as U.S. Pat. No. 5,899,938.

FIELD OF THE INVENTION

This invention relates to medical apparatus and methods in general, and more particularly to apparatus and methods for reconstructing ligaments.

BACKGROUND OF THE INVENTION

Ligaments are tough bands of tissue which serve to connect the articular extremities of bones, or to support or retain organs in place within the body. Ligaments are typically composed of coarse bundles of dense white fibrous tissue which are disposed in a parallel or closely interlaced manner, with the fibrous tissue being pliant and flexible, but not significantly extensible.

In many cases, ligaments are torn or ruptured as a result of accidents. As a result, various procedures have been developed to repair or replace such damaged ligaments.

For example, in the human knee, the anterior and posterior cruciate ligaments (i.e., the ACL and PCL) extend between the top end of the tibia and the bottom end of the femur. The ACL and PCL cooperate, together with other ligaments and soft tissue, to provide both static and dynamic stability to the knee. Often, the anterior cruciate ligament (i.e., the ACL) is ruptured or torn as a result of, for example, a sports-related injury. Consequently, various surgical procedures have been developed for reconstructing the ACL so as to restore normal function to the knee.

In many instances, the ACL may be reconstructed by replacing the ruptured ACL with a graft ligament. More particularly, with such procedures, bone tunnels are typically formed in the top end of the tibia and the bottom end of the femur, with one end of the graft ligament being positioned in the femoral tunnel and the other end of the graft ligament being positioned in the tibial tunnel. The two ends of the graft ligament are anchored in place in various ways known in the art so that the graft ligament extends between the femur and the tibia in substantially the same way, and with substantially the same function, as the original ACL. This graft ligament then cooperates with the surrounding anatomical structures so as to restore normal function to the knee.

In some circumstances the graft ligament may be a ligament or tendon which is harvested from elsewhere in the patient; in other circumstances the graft ligament may be a synthetic device. For the purposes of the present invention, all of the foregoing can be collectively referred to as a "graft ligament", "graft material" or "graft member."

As noted above, the graft ligament may be anchored in place in various ways. See, for example, U.S. Pat. No. 4,828,562, issued May 9, 1989 to Robert V. Kenna; U.S. Pat. No. 4,744,793, issued May 17, 1988 to Jack E. Parr et al.; U.S. Pat. No. 4,755,183, issued Jul. 5, 1988 to Robert V. Kenna; U.S. Pat. No. 4,927,421, issued May 22, 1990 to E. Marlowe Goble et al.; U.S. Pat. No. 4,950,270, issued Aug. 21, 1990 to Jerald A. Bowman et al.; U.S. Pat. No. 5,062,843, issued Nov. 5, 1991 to Thomas H. Mahony, III; U.S. Pat. No. 5,147,362, issued Sep. 15, 1992 to E. Marlowe Goble; U.S. Pat. No. 5,211,647, issued May 18, 1993 to Reinhold Schmieding; U.S. Pat. No. 5,151,104, issued Sep. 29, 1992 to Robert V. Kenna; U.S. Pat. No. 4,784,126, issued Nov. 15, 1988 to Donald H. Hourahane; U.S. Pat. No. 4,590,928, issued May 27, 1986 to Michael S. Hunt et al.; and French Patent Publication No. 2,590,792, filed Dec. 4, 1985 by Francis Henri Breard.

Despite the above-identified advances in the art, there remains a need for a graft ligament anchor which is simple, easy to install, and inexpensive to manufacture, while providing secure, trouble-free anchoring of the graft ligament, typically in the knee joint of a mammal.

OBJECTS OF THE INVENTION

Accordingly, one object of the present invention is to provide an improved graft ligament anchor which is relatively simple in construction and therefore inexpensive to manufacture, relatively easy to handle and install, and reliable and safe in operation.

Another object of the present invention is to provide an improved method for attaching a graft ligament to a bone.

SUMMARY OF THE INVENTION

These and other objects of the present invention are addressed by the provision and use of a novel graft ligament anchor comprising graft ligament engagement means for disposition in an opening in a bone, such that a wall of the graft ligament engagement means resides adjacent to at least one graft ligament disposed in the opening, and locking means for disposition in the opening in the bone and at least partially engageable with the graft ligament engagement means. The elements of the graft ligament anchor are adapted such that movement of the locking means in the opening in the bone causes at least a part of the locking means to engage the graft ligament engagement means so as to urge the graft ligament engagement means, and hence the portion of the graft ligament disposed adjacent thereto, toward a wall of the opening in the bone, whereby to secure the graft ligament to the wall of the opening.

In use, an opening is made in the bone, and the graft ligament and the graft ligament engagement means are inserted into the opening, with a portion of the graft ligament being disposed alongside a wall of the graft ligament engagement means. In accordance with the present invention, the locking means are also positioned in the opening in the bone, alongside the graft ligament engagement means, with the locking means being separated from the graft ligament by a portion of the graft ligament engagement means. The method further includes moving the locking means in the opening in the bone so as to cause at least a portion thereof to urge the graft ligament engagement means, and hence the portion of the graft ligament disposed adjacent thereto, toward a wall of the opening, whereby to secure the graft ligament to the wall of the opening.

In one aspect of the invention, a graft fixation device for fixing a graft member within a bone tunnel includes a radially expandable sheath having a side wall with at least one structurally weakened fracture region extending longitudinally along a length of the sheath in the side wall. The radially expandable sheath is sized to fit within a bone tunnel so that a graft member may be accommodated between a wall of a bone tunnel and an outer surface of the radially expandable sheath. A sheath expander is disposable in a central lumen of the radially expandable sheath to radially expand the sheath so as to fix the graft member within the bone tunnel. The structurally weakened fracture region is adapted to fracture upon radial expansion of the sheath to allow varying amounts of radial expansion.

In specific embodiments of this aspect of the invention, a number of longitudinal side wall segments can be provided, the segments being connected by longitudinal fracture regions. The side wall segments can also have concave outer surfaces so that each segment can capture a portion of graft material between its outer surface and the bone tunnel wall. In a further embodiment, the segments can be longitudinally divided into subsegments connected by longitudinal flexion regions.

In another aspect of the invention, a graft fixation device for fixing a graft member within a bone tunnel includes a radially expandable sheath having a side wall comprising a plurality of longitudinal side wall segments separated by convex longitudinal flex regions having convex outer surfaces, the radially expandable sheath being sized to fit within a bone tunnel and defining a central lumen. In this aspect, the side wall segments are flexible and have a concave outer surface adapted to enclose a graft member between the concave outer surface and a bone tunnel wall. A sheath expander is disposable in the central lumen of the radially expandable sheath to flex the convex longitudinal flex regions and the flexible concave wall segments to radially expand the sheath so as to fix a graft member within a bone tunnel.

In specific embodiments of this aspect, the side wall segments may include rigid longitudinal subsegments connected by longitudinal flex regions to provide flexing within the segments. In addition, convex longitudinal flex regions may be configured to flex, but then fracture to allow further radial expansion of the sheath.

Graft fixation devices of the invention allow a wider variety of materials to be used to form the radially expanding sheath and can also allow a single sized sheath to be used with a larger variety of bone tunnel and expander sizes.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 1 is a diagrammatic sectional view of one form of graft ligament anchor made in accordance with the present invention;

FIG. 2 is similar to FIG. 1, but shows the graft ligament anchor components in different operating positions;

FIG. 6 is a diagrammatic sectional view of another form of graft ligament anchor made in accordance with the present invention;

FIG. 7 is a diagrammatic sectional view of still another form of graft ligament anchor made in accordance with the present invention;

FIG. 8 is a diagrammatic sectional view of yet another form of graft ligament anchor made in accordance with the present invention;

FIG. 9 is a perspective view of one of the components of the graft ligament anchor shown in FIG. 8;

FIG. 13A is a diagrammatic sectional view of still another form of ligament anchor made in accordance with the present invention;

FIG. 14 is a top plan view of still another form of graft ligament anchor made in accordance with the present invention;

FIG. 15 is a side view, in section, of the graft ligament anchor shown in FIG. 14;

FIG. 16 is a side view showing the graft ligament anchor of FIGS. 14 and 15 securing a graft ligament to a bone;

FIG. 23 is a perspective view of components of the graft ligament anchor of FIG. 22;

FIG. 24 is a perspective view of a radially expandable sheath in accordance with a further embodiment of the invention;

DETAILED DESCRIPTION OF THE INVENTION

Figure 3:
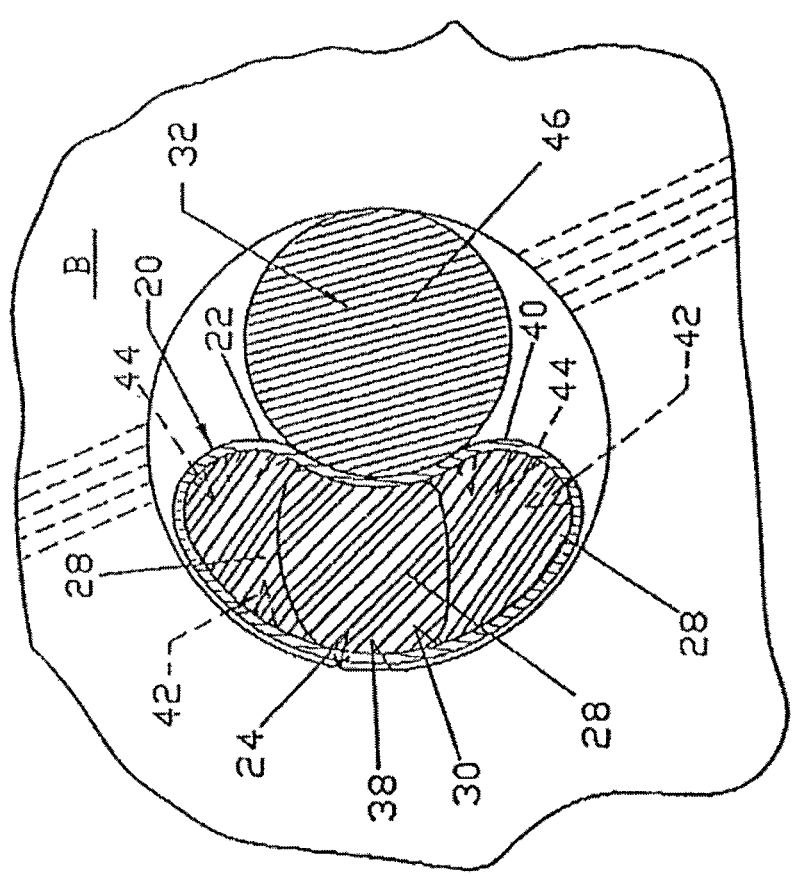
FIG. 3 is similar to FIG. 1, but shows an alternative embodiment of the present invention.

Referring first to FIG. 1, it will be seen that one illustrative embodiment of the present invention includes a graft ligament engagement means 20 comprising a deformable sleeve 22, preferably formed out of metal or plastic, and adapted to be inserted into an opening 24 formed in a bone B. One or more graft ligaments 28 are disposed alongside an interior wall 30 of sleeve 22.

The embodiment illustrated in FIG. 1 further includes locking means 32, which may be a pivotally movable rocker arm 34, which may be provided with a slot 36 for receiving a key member (not shown) for turning rocker arm 34.

Referring to FIG. 2, it will be seen that turning rocker arm 34 enables a portion of the rocker arm to impinge upon an exterior surface 40 of sleeve 22 so as to force sleeve 22, and hence graft ligaments 28 contained therein, toward sidewall 38 of opening 24, whereby to secure sleeve 22 and graft ligaments 28 between opening sidewall 38 and locking means 32.

In operation, opening 24 is first made in bone B and then graft ligaments 28 and graft ligament engagement means 20 are inserted into opening 24, with graft ligaments 28 being disposed alongside a first wall, i.e., the interior wall 30, of sleeve 22. Locking means 32 are inserted into opening 24 alongside the exterior surface 40 of sleeve 22. Locking means 32 are thus separated from graft ligaments 28 by graft ligament engagement means 20, i.e., sleeve 22. As noted above, movement of locking means 32 causes at least a portion thereof to engage sleeve 22 and to crimp the sleeve inwardly upon graft ligaments 28, and to push both sleeve 22 and graft ligaments 28 against sidewall 38 of opening 24.

If it is desired to thereafter release graft ligaments 28, rocker arm 34 may be moved back to the position shown in FIG. 1. To this end, graft ligament engagement means 20 preferably are formed out of a resilient material, whereby engagement means 20 can return to substantially the same position shown in FIG. 1 when locking means 32 return to the position shown in FIG. 1.

If desired, substantially all of sleeve 22 can be formed so as to be deformable; alternatively, some of sleeve 22 can be formed so as to be rigid. By way of example, the portion of sleeve 22 contacted by locking means 32 can be formed so as to be substantially rigid.

Graft ligaments 28 may comprise natural or synthetic graft ligament material, and the anchor can be used to attach natural or synthetic graft ligaments and/or tendons to bone. Sleeve 22 preferably is provided with inwardly-extending protrusions 42, such as spikes 44, for securely retaining graft ligaments 28 therein.

Locking means 32 may be a rocker arm type, such as the rocker arm member 34 shown in FIGS. 1 and 2, or a generally conically-shaped expansion plug 46, as shown in FIG. 3, with the expansion plug preferably being threaded such that as the plug is screwed into place, an increasing diameter of the plug engages sleeve 22 in a wedge-like manner so as to force the sleeve against interior wall 38 of opening 24.

Figure 4:
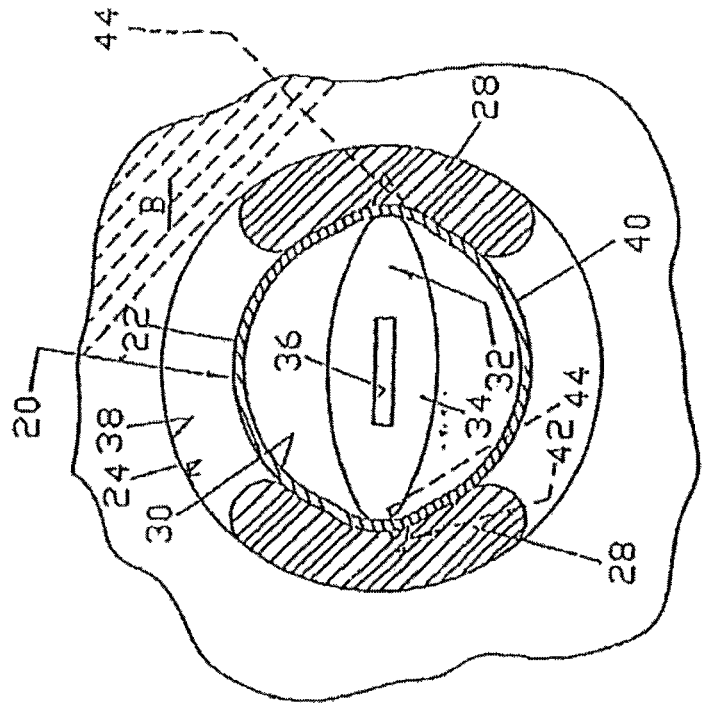
FIG. 4 is a diagrammatic sectional view of another form of graft ligament anchor made in accordance with the present invention.

In FIG. 4, there is shown an alternative embodiment in which graft ligaments 28 are disposed alongside exterior wall 40 of sleeve 22, and locking means 32 is disposed within sleeve 22. With this embodiment, locking means 32 operate to engage interior wall 30 of the sleeve (FIG. 5), whereby to force graft ligaments 28 against sidewall 38 of opening 24. Again, locking means 32 may be a rocker arm type, such as the rocker arm member 34 shown in FIGS. 4 and 5, or may be an expansion plug 46, preferably threaded, of the sort shown in FIG. 3. With the embodiment shown in FIGS. 4 and 5, sleeve 22 may be provided with protrusions 42 (in the form of spikes 44, for example) on the exterior wall 40 thereof for engagement with graft ligaments 28. In many instances, it is beneficial to provide at least two discrete graft ligaments 28 and, in such cases, it is preferable that the graft ligaments be disposed on substantially opposite diametric sides of the sleeve, as shown in FIGS. 4 and 5.

Figure 5:
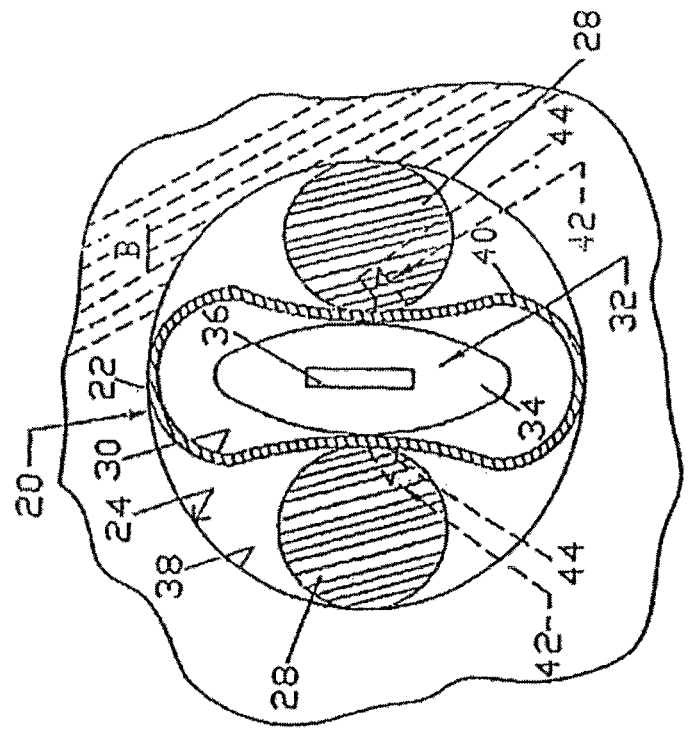
FIG. 5 is similar to FIG. 4, but shows the graft ligament anchor components in different operating positions.

In FIG. 6, there is shown an embodiment similar to that shown in FIGS. 4 and 5, but provided with an expandable sleeve 22A, rather than a deformable metal or plastic sleeve 22 as shown in FIGS. 1-5. Sleeve 22A may be formed out of an elastomeric material, and it is expanded radially outwardly by engagement with a centrally disposed locking means 32 (preferably in the form of a threaded expansion plug 46) so as to force graft ligaments 28 outward into a secured position between sleeve 22A and opening sidewall 38.

In operation, the embodiments shown in FIGS. 4-6 function similarly to the embodiments shown in FIGS. 1-3 in attaching graft ligaments 28 to bone B. Opening 24 is first made in bone B. Graft ligaments 28 and graft ligament engagement means 20 (in the form of sleeve 22 or sleeve 22A) are inserted into opening 24, with graft ligaments 28 disposed alongside exterior wall 40 of the graft ligament engagement means, i.e., alongside the exterior wall 40 of sleeve 22 or sleeve 22A. Locking means 32 (in the form of a rocker arm member 34 or a threaded expansion plug 46) are inserted axially into the sleeve, alongside interior wall 30 of the sleeve. Locking means 32 are thus separated from the graft ligaments 28 by the sleeve (22 or 22A). Then locking means 32 are manipulated so as to engage the sleeve (22 or 22A) and thereby urge the sleeve, and hence graft ligaments 28, toward opening sidewall 38, whereby to secure the sleeve and graft ligaments to the wall of the opening.

If and when it is desired to adjust tension on graft ligaments 28, locking means 32 may be backed off, that is, if locking means 32 comprise the rocker arm type cam member 34, the arm need only be rotated 90° from the positions shown in FIGS. 2 and 5, to return to the positions shown, respectively, in FIGS. 1 and 4; if, on the other hand, locking means 32 comprise expansion plug 46, the plug need only be unscrewed or otherwise axially withdrawn so as to release the securing of the graft ligaments.

Referring next to FIG. 7, it will be seen that in an alternative embodiment, graft ligament engagement means 20 comprises plate means 48 which are movable transversely within the bone opening. As in the embodiments previously described, graft ligaments 28 are disposed alongside a wall 50 of graft ligament engagement means 20, which in this instance is a first major surface of plate means 48. Graft ligament engagement means 20 are disposed between graft ligaments 28 and locking means 32. Locking means 32 may be, as in the above-described embodiments, an expansion plug 46 (as shown in FIG. 7), or locking means 32 may be a rocker arm type of cam member 34 (of the sort shown in FIGS. 1, 2, 4 and 5). Locking means 32 are adapted to impinge upon a second major surface 52 of plate means 48. Plate means 48, in the embodiment shown in FIG. 7, comprises a single plate 54 having, on first major surface 50 thereof, one or more concavities 56 for nesting one or more graft ligaments 28, respectively.

In the attachment of one or more graft ligaments 28 to a bone B, using the embodiment of FIG. 7, locking means 32 are manipulated so as to bear against plate 54 so as to move plate 54 into engagement with graft ligaments 28, and thence to further move plate 54 so as to secure the graft ligaments against sidewall 38 of opening 24.

Referring next to FIG. 8, it will be seen that locking means 32 may comprise the threaded expansion plug 46 deployed partly in opening 24 and threaded partly into bone B, thus serving as a so-called interference screw. With this arrangement, plug 46 is thereby (i) in part along its length disposed in opening 24, protruding into the opening from opening wall 38, and (ii) in part along its length threadedly engaged with bone B. Screwing in plug 46 causes the plug to engage plate 54 which, in turn, compacts one or more graft ligaments 28 against wall 38 of opening 24.

In lieu of, or in addition to, the aforementioned concavities 56 shown in FIG. 7, plate 54 may be provided with gripper ribs 58 for engaging graft ligaments 28, as shown in FIGS. 8 and 9.

Figure 10:
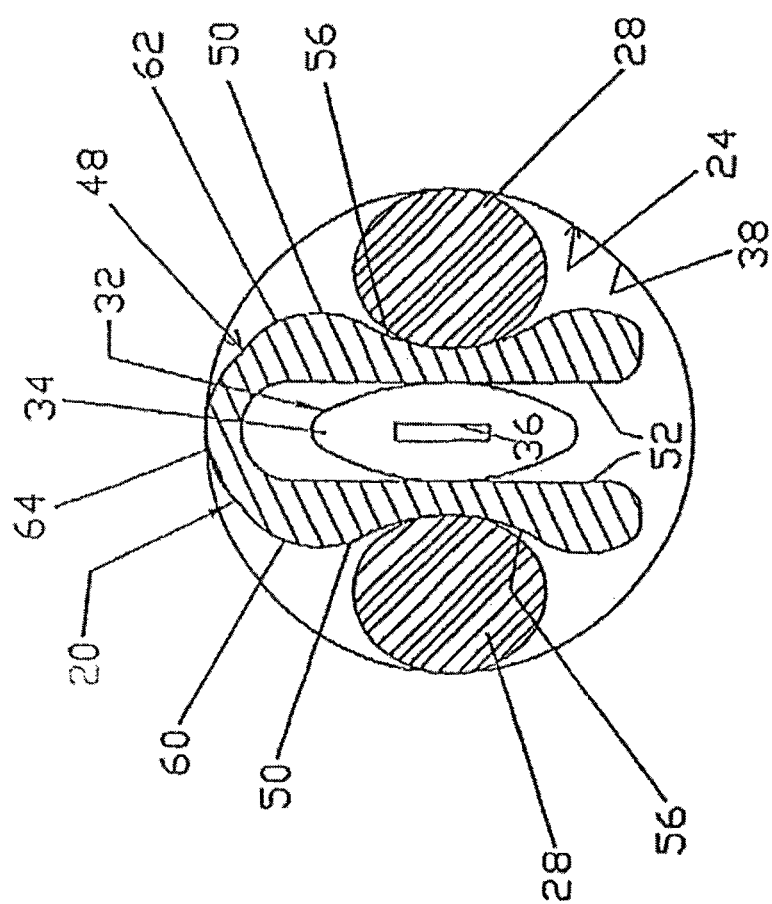
FIG. 10 is a diagrammatic sectional view of still another form of graft ligament anchor made in accordance with the present invention.

In FIG. 10, it is shown that plate means 48 may include first and second plates 60, 62, each having a wall 50 facing one or more graft ligaments 28, and a wall 52 facing locking means 32. Plates 60, 62 may be joined together by a link 64 which may be molded integrally with plates 60, 62 so as to form a so-called "living hinge" link. Locking means 32 are depicted in FIG. 10 as a rocker arm type of cam member 34, but it will be appreciated that an expansion plug type of locking means (e.g., a plug 46 such as that shown in FIGS. 3, 6 and 7) might also be used.

In operation, rotative movement of rocker arm 34 (or axial movement of expansion plug 46) causes plates 60, 62 to move outwardly from each other so as to urge graft ligaments 28 against wall 38 of opening 24. Walls 50 of plates 60, 62 may be provided with concavities 56, as shown in FIG. 10, or with ribs 58 of the sort shown in FIG. 9, or both.

Figure 11:
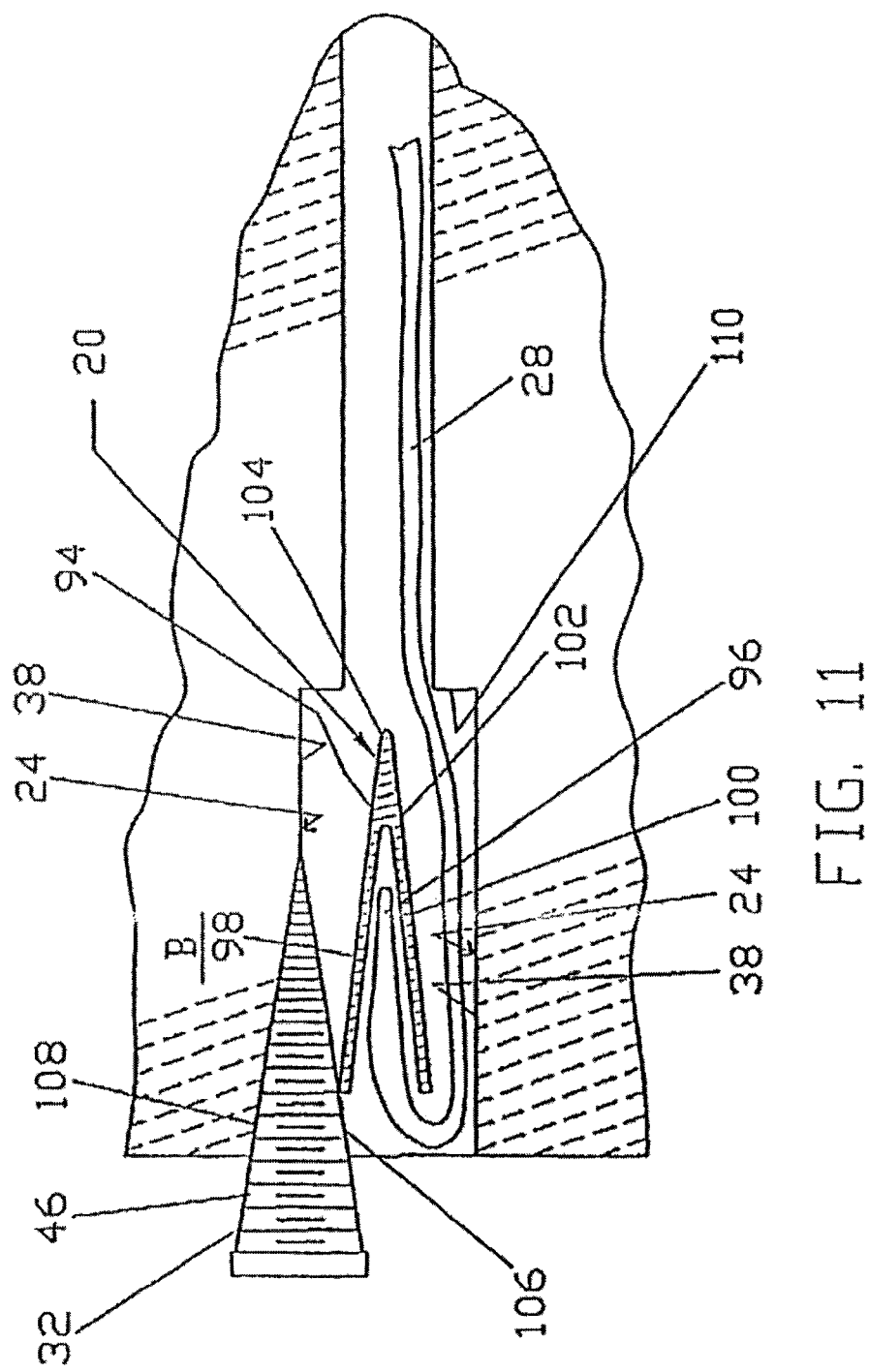
FIG. 11 is a diagrammatic view of still another form of graft ligament anchor made in accordance with the present invention.

Referring next to FIG. 11, it will be seen that still another embodiment of the present invention includes, as graft ligament engagement means 20, a V-shaped strip 94, preferably made out of a resilient metal or plastic material. An end portion 96 of a graft ligament 28 is disposed between first and second leg portions 98, 100 of V-shaped strip 94, and graft ligament 28 extends alongside an exterior surface 102 of second leg portion 100. Locking means 32 comprise a threaded expansion plug 46 disposed partly in opening 24 and partly in bone B, along sidewall 38 of opening 24, in a manner similar to the disposition of threaded expansion plug 46 shown in FIG. 8.

Upon screwing in expansion plug 46, the expansion plug engages first leg 98 of graft ligament engagement means 20 (i.e., the V-shaped strip 94) to force first leg 98 to close upon second leg 100 with the graft ligament end portion 96 sandwiched therebetween and, upon further screwing in of threaded expansion plug 46, to force graft ligament engagement means 20 and graft ligament 28 against wall 38 of opening 24. To release graft ligament 28, an operator need only back out expansion plug 46.

When attaching a graft ligament to a bone with the graft ligament anchor shown in FIG. 11, an opening is first drilled, or otherwise made, in the bone. Then the V-shaped strip 94 is inserted into the opening, with a nose portion 104 thereof pointed inwardly of the bone. Next, end portion 96 of graft ligament 28 is inserted between first and second leg portions 98, 100 of V-shaped strip 94. Threaded expansion plug 46 is then inserted into opening wall 38 such that a first portion 106 of the lengthwise extent of plug 46 is disposed in opening 24, and second portion 108 of the lengthwise extent of plug 46 is threadedly engaged with bone B. Expansion plug 46 is then screwed further down so as to cause plug 46 to engage first leg 98 of V-shaped strip 94 so as to secure graft ligament end portion 96 in V-shaped strip 94, and then screwed down further to wedge strip 94 and graft ligament 28 against wall 38 of opening 24.

Still referring to FIG. 11, it is to be appreciated that bone opening 24 may be formed with a constant diameter throughout its length or, if desired, may be formed with two different diameters along its length, in the manner shown in FIG. 11, so as to form an annular shoulder 110 within the bone opening The provision of an annular shoulder 110 can be very helpful in ensuring that the graft ligament anchor is prevented from migrating further into bone B, even if graft ligament 28 should thereafter be subjected to substantial retraction forces.

In a modification (not shown) of the FIG. 11 embodiment, the expansion plug 46 may be entered alongside graft ligament 28 and second leg portion 100 of strip 94. In this modified version, the expansion plug 46 operates as described above, except that expansion plug 46 engages graft ligament 28 and forces strip first leg 98 against wall 38 of opening 24.

Figure 12:
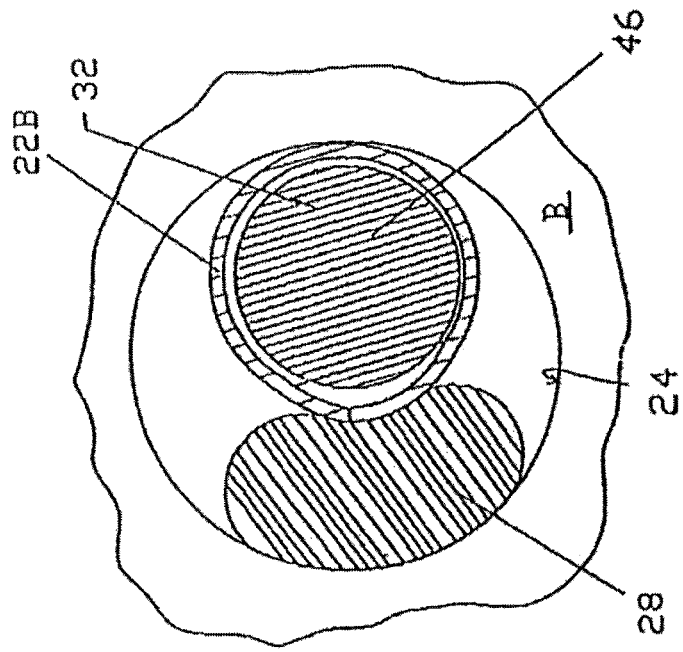
FIG. 12 is a diagrammatic sectional view of yet another form of graft ligament anchor made in accordance with the present invention.
Figure 13:
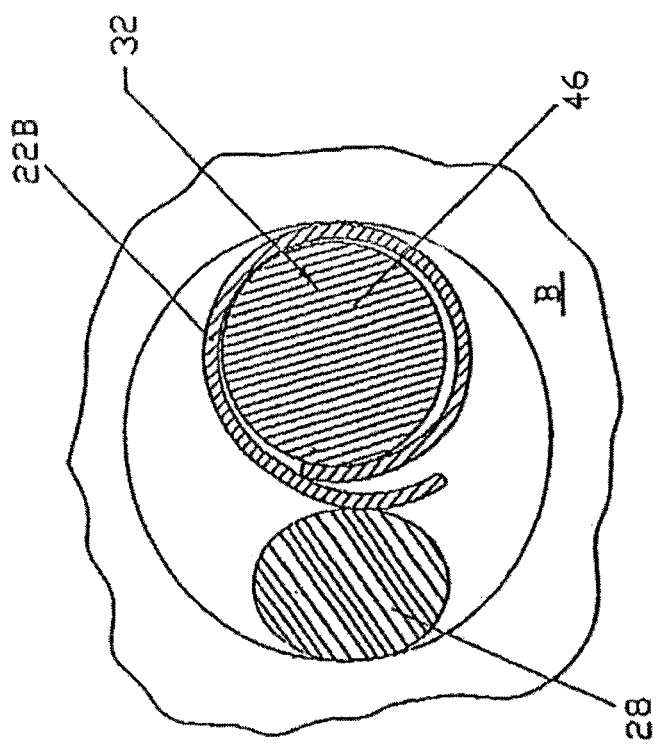
FIG. 13 is similar to FIG. 12, but shows the graft ligament anchor components in different operating conditions.

Looking next at FIGS. 12 and 13, yet another form of graft ligament anchor is disclosed. This graft ligament anchor is similar to the embodiment shown in FIG. 6, except that the expandable sleeve 22B is in the form of a cylindrical coil. Sleeve 22B is formed out of an elastomeric material and is expanded radially outwardly by engagement with a centrally disposed locking means 32 (preferably an axially-movable threaded expansion plug 46) so as to force graft ligament 28 outward into a secured position between sleeve 22B and bone B.

In FIG. 13A there is shown an embodiment similar to that shown in FIG. 10, but in which the first and second plates 60, 62 are discrete plates and not connected to each other. With this arrangement, locking means 32 is inserted into a central recess 74 defined by plate walls 52, and may comprise either an expansion plug 46 of the type shown in FIGS. 6 and 7 or a rocker arm type of cam member 34 of the type shown in FIGS. 1 and 2.

Looking next at FIGS. 14 and 15, another graft ligament anchor 200 is shown. Anchor 200 includes graft ligament engagement means 20 comprising a flat plate 201, a pair of through-holes 202, 204 and a threaded through-hole 206. In use, and looking now at FIGS. 14, 15 and 16, the free end 96 of graft ligament 28 is passed downward through hole 202 and then back upward again through hole 204, and then a screw 208 is used to secure anchor 200 to the wall 210 of the bone opening by threading the shank of screw 208 through hole 206, through graft ligament 28, and into bone B. This will cause screw 208 and plate 201 to securely attach graft ligament 28 to bone B.

Figure 17:
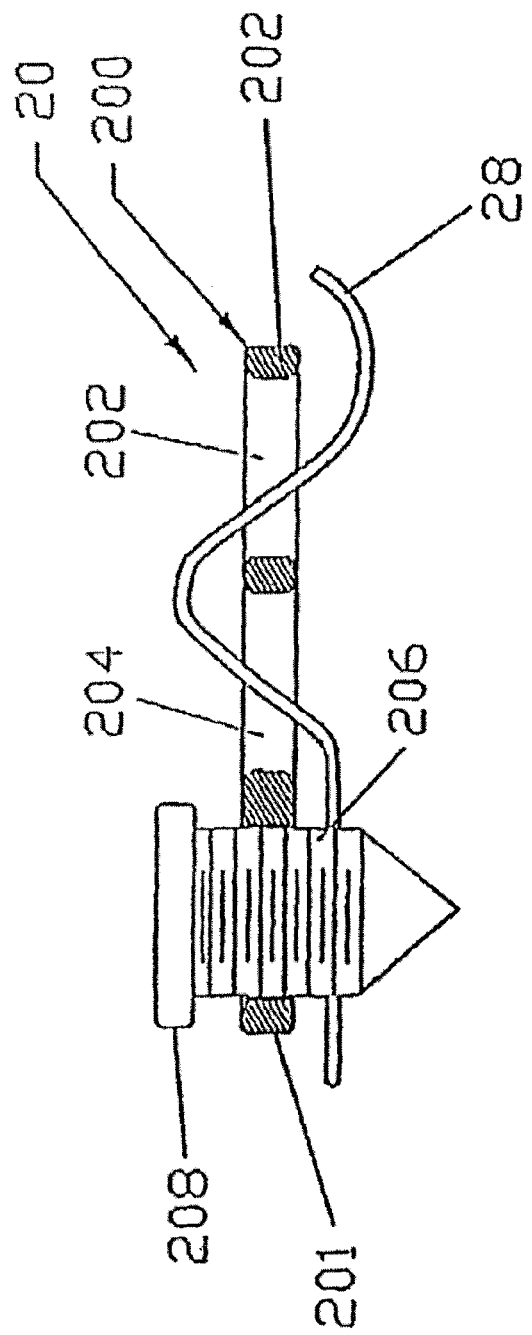
FIG. 17 is similar to a portion of FIG. 16, but showing components of the graft ligament anchor and graft ligament of FIG. 16 in alternative positions.

As shown in FIG. 17, alternatively, graft ligament 28 may be passed upwardly through hole 202 and downwardly through hole 204. Screw 208 is then threaded through hole 206 and graft ligament 28 and into bone B. Thus, as in the embodiment shown in FIG. 16, screw 208 and plate 201 secure graft ligament 28 to bone B.

Figure 18:
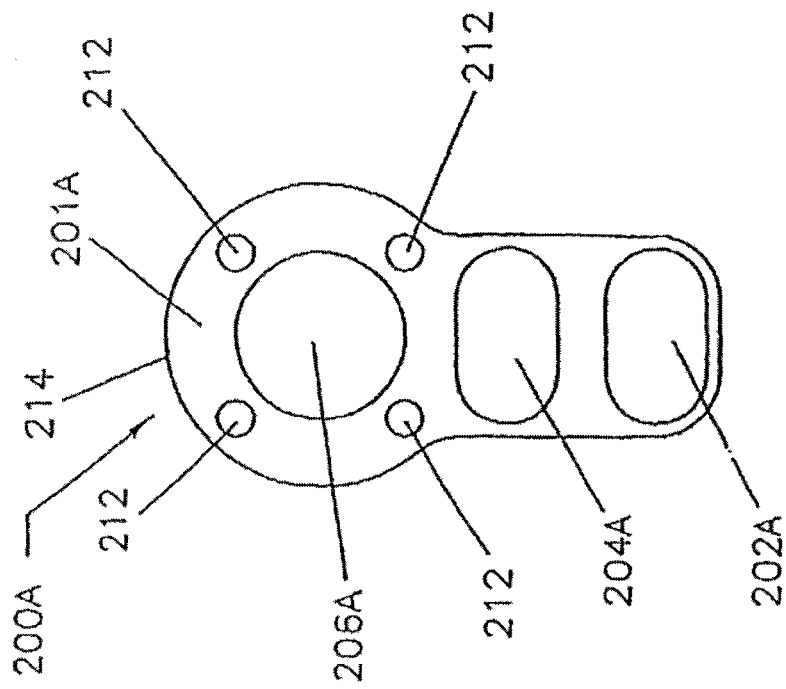
FIG. 18 is a top plan view of yet another form of graft ligament anchor made in accordance with the present invention.
Figure 19:
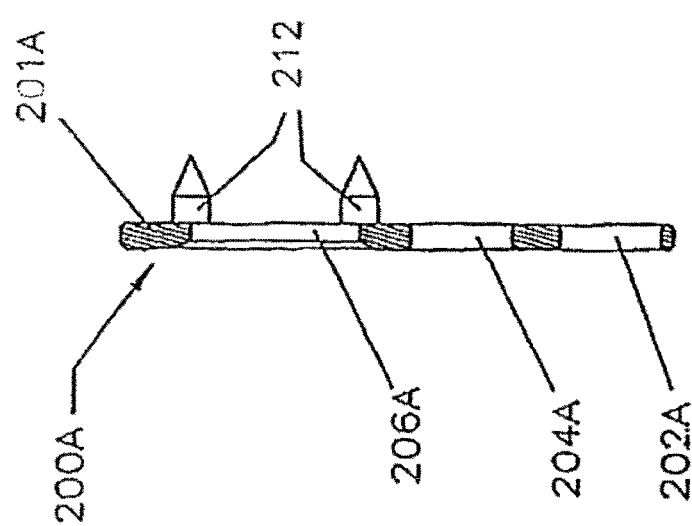
FIG. 19 is a side view, in section, of the graft ligament anchor shown in FIG. 18.

FIGS. 18 and 19 show another graft ligament anchor 200A. Graft ligament anchor 200A is similar to graft ligament anchor 200, except that it includes a plurality of spikes 212 for projecting into wall 210 (FIG. 16) of bone B when the graft ligament anchor is deployed against the bone. Also, graft ligament anchor 200A has an enlarged configuration 214 in the region of through-hole 206A, as shown in FIG. 18.

Figure 20:
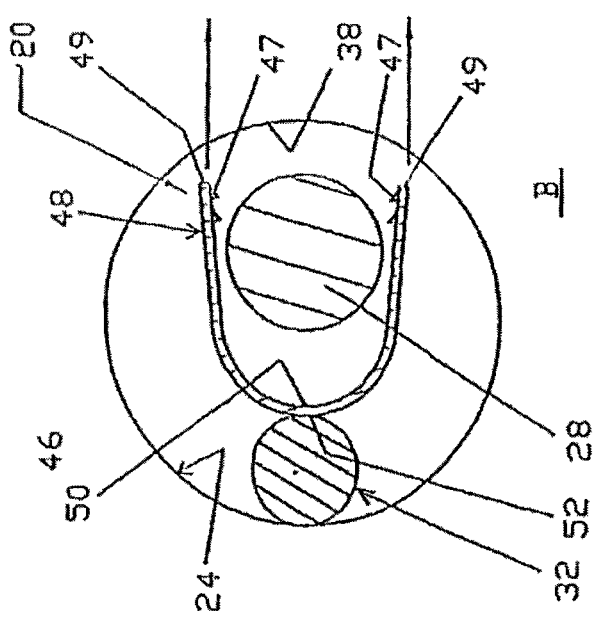
FIG. 20 is a diagrammatic sectional view of still another form of graft ligament anchor made in accordance with the present invention.
Figure 21:
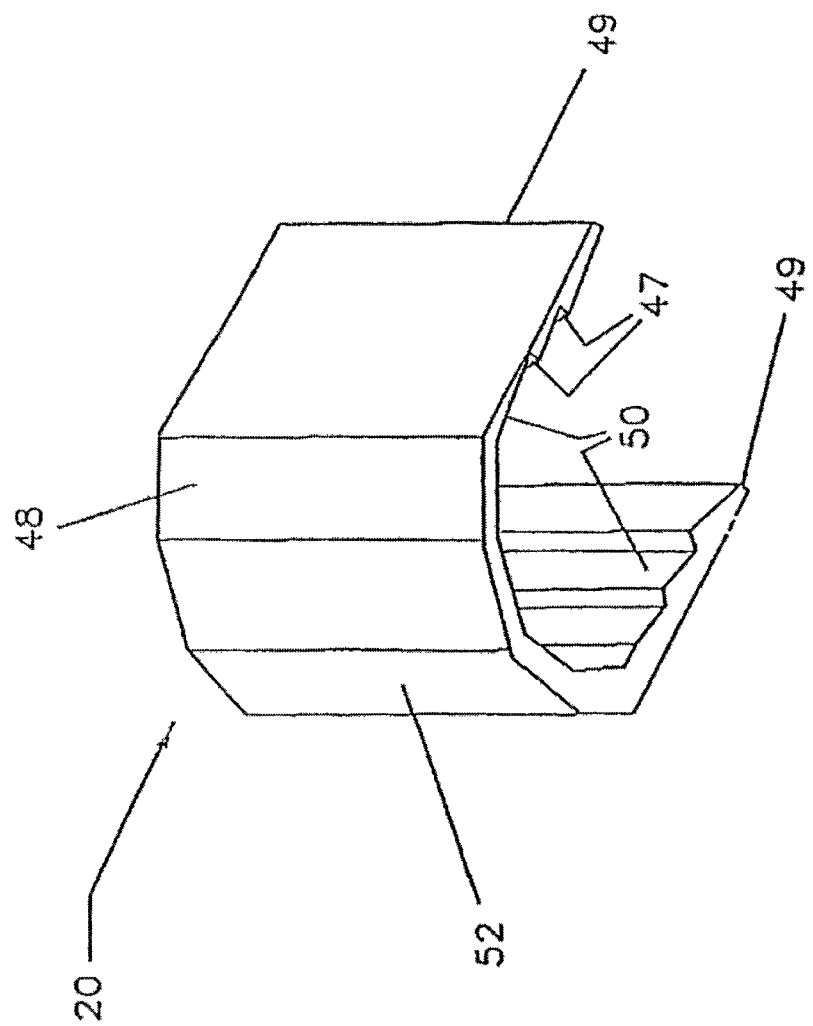
FIG. 21 is a perspective view of a component of the graft ligament anchor shown in FIG. 20.

Referring next to FIG. 20, there is shown a still further alternative embodiment of graft ligament anchor, similar to that shown in FIG. 7, wherein graft ligament engagement means 20 comprises plate means 48 formed in a U-shaped configuration (FIG. 21) movable transversely within bone opening 24. At least one graft ligament 28 is disposed alongside wall 50 of graft ligament engagement means 20, which in this instance is a first major surface of plate means 48. Graft ligament engagement means 20 is disposed between graft ligament 28 and locking means 32. Locking means 32 may be an expansion plug 46, as shown in FIG. 20 and in FIG. 7, or a rocker arm type cam member 34, as shown in FIG. 1, or an interference screw type expansion plug 46, as shown in FIG. 11, or a transverse screw 208, as shown in FIG. 16.

In attachment of one or more graft ligaments 28 to a bone B, using the embodiment of FIG. 20, locking means 32 is manipulated so as to bear against a second major surface 52 of plate means 48 and thereby move plate means 48 into engagement with graft ligament 28, and thence to drive free ends 49 of plate means 48 into sidewall 38 of opening 24 so as to fasten graft ligament 28 to sidewall 38 and, thereby, to bone B.

Figure 22:
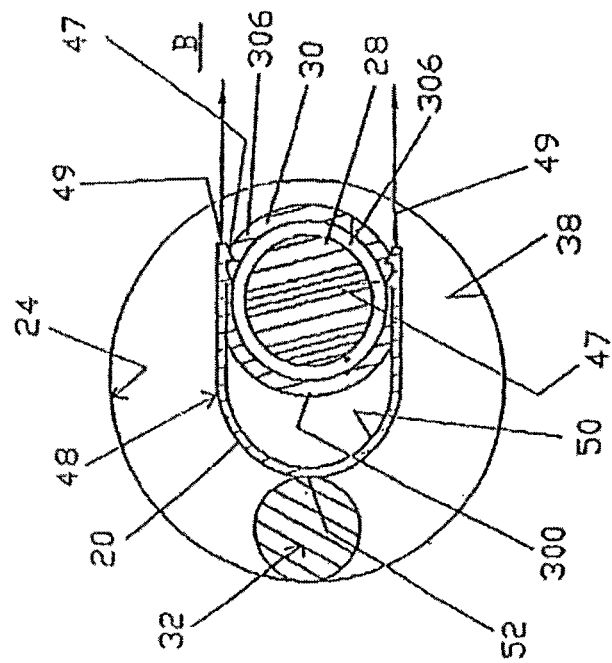
FIG. 22 is a diagrammatic sectional view of still another form of graft ligament anchor made in accordance with the present invention.

Referring to FIGS. 22 and 23, there is shown still another alternative embodiment of graft ligament anchor including a tubular member 300, open at first and second ends 302, 304 and having an opening 306 in the sidewall thereof. Otherwise, the graft ligament anchor of FIG. 22 is similar to the graft ligament anchor of FIG. 20, described hereinabove.

In attachment of one or more graft ligaments 28 to a bone, using the embodiment of FIGS. 22 and 23, locking means 32 are manipulated to bear against second major surface 52 of plate means 48 so as to move plate means 48 through tubular member opening 306 and into engagement with graft ligament 28, and thence further to drive free ends 49 of plate means 48 into sidewall 38 of opening 24, whereby to fasten tubular member 300 and graft ligament 28 to sidewall 38 and, thereby, to bone B. In this embodiment, and in the embodiments shown in FIGS. 1-3, an operator may fasten the graft ligament to the bone without the graft ligament contacting the bone. The tubular member 300 preferably is of a plastic or metallic material and the plate means 48 is of a plastic or metallic material. In the embodiments shown in FIGS. 20 and 22, the plate means 48 may be provided with interior teeth 47 for gripping graft ligament 28.

Figure 27:
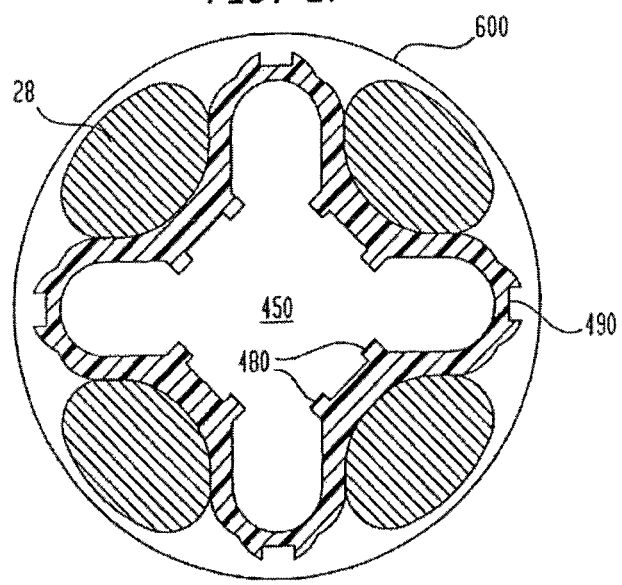
FIG. 27 is a cross-sectional view of the radially expandable sheath of FIG. 24 with graft material placed in a bone tunnel prior to fixation.
Figure 28:
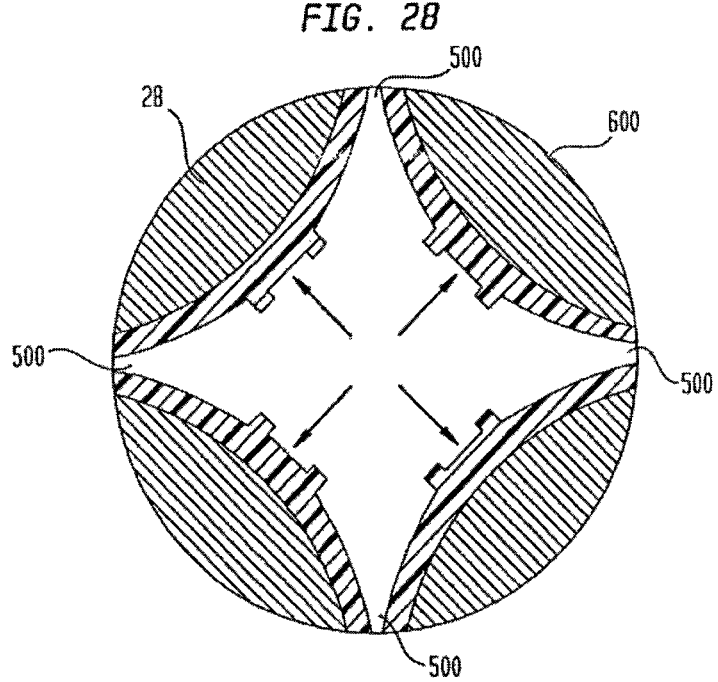
FIG. 28 is a cross-sectional view of the sheath and graft material of FIG. 27 in after fixation within the bone tunnel.

A further embodiment of the present invention is illustrated in FIG. 24-FIG. 28. FIG. 24 shows a perspective view of a selectively radially expandable sheath 400 having a side wall 401 and defining a central lumen 450. As illustrated in FIG. 27, sheath 400 is sized to fit within a bone tunnel 600 (FIG. 27) while capturing graft material 28 between an outer surface of the sheath and an inner wall of bone tunnel 600. Central lumen 450 is sized to accept a sheath expanding element (such as sheath expanding element 700 (FIG. 26) or locking means 32 (see, e.g., FIG. 10)) that expands the sheath radially to fix graft material 28 within bone tunnel 600 as illustrated in FIG. 28.

Referring again to FIG. 24, sheath 400 can include a proximal or "sheath expander lead-in" end region 403 that is tapered to ease insertion of a sheath expander into central lumen 450. Lead-in region 403 may have proximal cut-out areas 406 to facilitate radial expansion in the proximal cross-section of sheath 400. Central lumen 450 may also include female threads 407 on an inside surface 408 of side wall 401 to facilitate a threaded engagement with a threaded sheath expander (such as tapered screw sheath expander 700 (FIG. 26)) in central lumen 450. Lead-in region 403 of sheath 400 can also include a tab 1000 which may serve as a stop to prevent any overinsertion of sheath 400 into a bone tunnel. The outer diameter of side wall 401 may also taper from a larger diameter in lead-in region 403 to a smaller diameter at distal tip 409 to provide a gradual transition in the amount of ultimate compressive load being applied to graft members 28 during insertion. As with lead-in region 403, distal tip 409 may have cut-out areas 452 to facilitate radial expansion in the distal cross-section of sheath 400. A portion of the outside surface of side wall 401 may include ribs 402, protrusions or other similar features which roughen the outside surface and engage with either or both the wall 600 (FIGS. 27 and 28) of a bone tunnel and graft material 28 when sheath 400 is expanded.

Figure 25A:
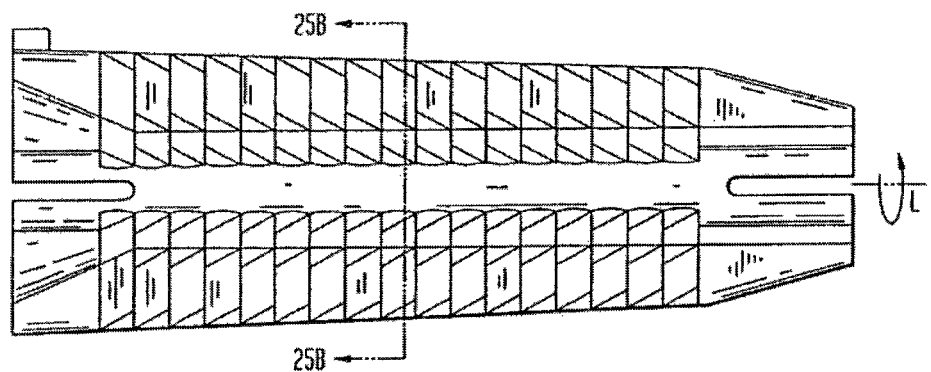
FIG. 25A is a side view of the sheath of FIG. 24.
Figure 25B:
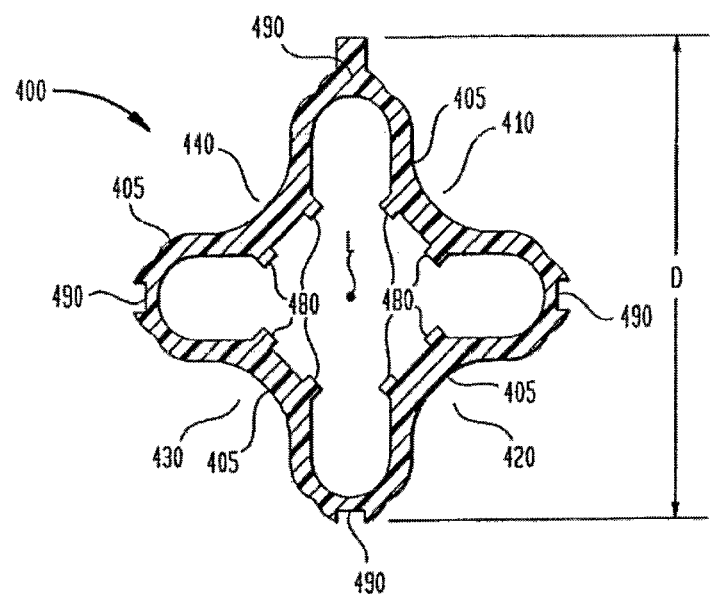
FIG. 25B is a cross-sectional view of the sheath of FIG. 25A taken along line A-A' in an unexpanded state.
Figure 26:
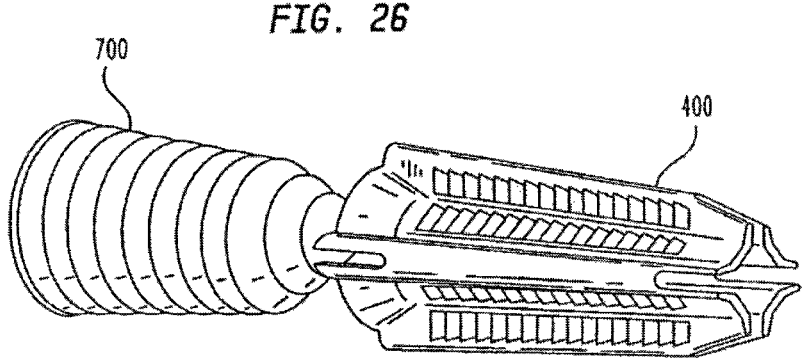
FIG. 26 is an exploded view of the radially expandable sheath of FIG. 24 and a sheath expander.

As illustrated in the cross-sectional view of FIG. 25B, side wall 401 of sheath 400 is divided into four londitudinal side wall segments 405, each having concave outer surfaces which provide regions 410, 420, 430, and 440 where graft material may be disposed between the side wall segments and bone tunnel wall 600 (as further illustrated in FIG. 27). In accordance with the principles of the invention, a sheath expander (such as tapered screw sheath expander 700) may be inserted into central lumen 450 of sheath 400 to deform non-circular side wall 401 toward a circular geometry to conform with an outer diameter of expander 700. Sheath 400 includes a number of features configured to accommodate this deformation.

In particular, sheath 400 can include one or more structurally weakened fracture regions 490 extending longitudinally along a length of side wall 401. As used herein, structurally weakened refers to a feature that can allow flexion and/or fracture side wall 401, in some instances allowing the wall to flex as if it were hinged (and it is further contemplated that a hinge of any type could be a structurally weakened region). In a preferred embodiment, fracture regions 490 extend substantially along or entirely along the length of side wall 401 and may incorporate proximal and distal cut outs 406 and 452. Further, fracture regions 490 may be configured to flex to allow some radial expansion of the sheath before fracturing to allow even further radial expansion of sheath 400 (post fracture expansion is illustrated in FIG. 28). Fracture regions 490 may be formed by thinning the material of side wall 401 longitudinally in the region of desired fracture, and in one embodiment, may be a longitudinal groove cut into side wall 401.

In the illustrative embodiment of FIG. 25B, sheath 400 comprises four longitudinal side wall segments 405 that circumscribe central lumen 450, each of the longitudinal side wall segments being connected to its neighbors by the four structurally weakened longitudinal fracture regions 490. While this configuration may be preferred in the situation that the graft material being fixed to a bone tunnel can easily be separated into four components, a person of ordinary skill in the art will recognize that more or fewer side wall segments and structurally weakened regions can be provided to adapt sheath 400 to different fixation requirements. In addition, central lumen need not be fully circumscribed by side wall segments having concave outer surfaces. For example, half of side wall 401 could take the form of one half of a cylinder generally conforming to the shape of the bone tunnel, while the other half of side wall 401 could comprise two or more side wall segments 405 having concave outer surfaces, the side wall segments 405 being connected to each other and to the half cylinder portion by longitudinal fracture regions. Such a configuration may be preferable where a surgeon wishes to fix the graft material to one side of a bone tunnel (such as an anterior or posterior side) at the expense of fixation to the opposed side.

Concave side wall segments 405 may also include longitudinal flexion regions 480 to aid in allowing the wall segments to expand radially outward to fix graft material to a bone tunnel wall. As with fracture regions 490, flexion regions can extend substantially along or entirely along the length of side wall 401. Flexion regions 480 may also be formed by thinning the material of side wall 401 longitudinally in the region of desired flexion, and in one embodiment, may be a longitudinal groove cut into side wall 401.

In the illustrated embodiment, each concave side wall segment 405 includes two longitudinal flexion regions 480 which divide the wall segments into three relatively rigid longitudinal subsegments connected by the two longitudinal flexion regions. A person of ordinary skill in the art will recognize that a sheath of the invention could be formed using only one flexion region within a wall segment or by using more than two such flexion regions within the spirit of the invention.

In one embodiment of the invention, longitudinal fracture regions 490 (which preferably flex before fracturing) have a convex outer surface and act as "outer hinges," while longitudinal flexion regions 480 act as "inner hinges" to allow a first measure of radial expansion toward a circular geometry by flexing of these inner and outer hinges. This first measure of radial expansion can be followed by fracture of one or more of the longitudinal fracture regions 490 to provide a second measure of radial expansion beyond the first measure.

The provision of inner 480 and outer 490 hinges in sheath 400 provides resiliency and malleability to side wall 401 and allows for the option of using stiffer, stronger starting stock for sheath 400 than would otherwise be possible. Both inner hinge flexion regions 480 and outer hinge fracture regions 490 serve as concentrated bending areas. However, fracture regions 490 are preferably configured to act as regions of maximum stress as there is less or no graft material 28 to counterbalance radial stresses. If side wall 401 is to fail at any location for lack of ductility or strength, this embodiment allows for breakage to occur at fracture regions 490, further illustrated in FIG. 28 after fracture as edges 500. Flexion regions 480, as thinned regions, are preferably configured to add flexibility to side wall segments 405 and to facilitate increase of the radius of curvature of the concave outer surface of segments 405 without undue risk of breakage on segments 405 which must carry a compressive load to graft material 28. Accordingly, fracture regions 490 would preferably have a geometry such that the local material stresses during expansion of sheath 400 are always greater than the local stresses at flexion regions 480 so that material rupture will always be directed along the path of fracture regions 490. This means of controlled rupture ensures that sheath 400 will remain biomechanically functional since the rupture will then occur away from ligament accommodating regions 410, 420, 430, 440.

Further, such controlled rupture along fracture regions 490 facilitates use of a wider variety of expander sizes, including the use of expanders having an outer diameter or circumference at least as large as the diameter or circumference of sheath 400. In this way, a single sheath size may be stocked for a wide variety of procedures and intended bone tunnel sizes. In one embodiment, sheath 400 may be provided in a kit to surgeons in which a plurality of expanders having different sizes are provided for use with a single size sheath.

The inclusion of fracture regions 490 and/or flexion regions 480 widen the choice of available sheath materials to include, for example, biocompatible bioabsorbable polymers selected from the group consisting of aliphatic polyesters, polyorthoesters, polyanhydrides, polycarbonates, polyurethanes, polyamides and polyalkylene oxides. Sheath 400 may also be formed from absorbable glasses and ceramics (possibly comprising calcium phosphates and other biocompatible metal oxides (i.e., CaO)). Sheath 400 may also be formed from metals; it can comprise combinations of metals, absorbable ceramics, glasses or polymers.

In further embodiments, the expandable sheath may be fabricated from aliphatic polymer and copolymer polyesters and blends thereof. Suitable monomers include but are not limited to lactic acid, lactide (including L-, D-, meso and D,L mixtures), glycolic acid, glycolide, E-caprolactone, p-dioxanone (1,4-dioxan-2-one), trimethylene carbonate (1,3-dioxan-2-one), delta-valerolactone, beta-butyrolactone, epsilon-decalactone, 2,5-diketomorpholine, pivalolactone, alpha, alpha-diethylpropiolactone, ethylene carbonate, ethylene oxalate, 3-methyl-1,4-dioxane-2,5-dione, 3,3-diethyl-1,4-dioxan-2,5-dione, gamma-butyrolactone, 1,4-dioxepan-2-one, 1,5-dioxepan-2-one, 6,6-dimethyl-dioxepan-2-one, 6,8-dioxabicycloctane-7-one and combinations thereof. These monomers generally are polymerized in the presence of an organometallic catalyst and an initiator at elevated temperatures. The organometallic catalyst may be tin based, (e.g., stannous octoate), and may be present in the monomer mixture at a molar ratio of monomer to catalyst ranging from about 10,000/1 to about 100,000/1. The aliphatic polyesters are typically synthesized in a ring-opening polymerization process. The initiator is typically an alkanol (including diols and polyols), a glycol, a hydroxyacid, or an amine, and is present in the monomer mixture at a molar ratio of monomer to initiator ranging from about 100/1 to about 0.5000/1. The polymerization typically is carried out at a temperature range from about 80° C. to about 240° C., preferably from about 100° C. to about 220° C., until the desired molecular weight and viscosity are achieved.

It is to be understood that the present invention is by no means limited to the particular constructions and methods herein disclosed and/or shown in the drawings, but also comprises any modifications or equivalents within the scope of the claims

What is claimed is:

1. A graft ligament anchor system for fixing a graft ligament within a bone tunnel having a circumferential wall and an opening, comprising:
    a graft ligament fixing element for disposition within the bone tunnel, the graft ligament fixing element having a plurality of side wall portions configured to contact a graft ligament portion when the graft ligament is placed in the bone tunnel, the side wall portions including at least two concavities extending longitudinally and configured to nest graft ligament portions when a graft ligament is placed in the bone tunnel;
    a graft ligament, the graft ligament being in contact with the side wall; and
    a locking element configured for placement within the bone tunnel and to engage the graft ligament fixing element, the locking element being separated from the graft ligament by the graft ligament fixing element;
    wherein a first side and a second side of the side wall portions are deformable and movement of the locking element causes a change in shape in the first side and the second side;
    wherein the locking element and graft ligament fixing element are further configured so that movement of the locking element urges the side wall of the graft ligament fixing element, and hence the graft ligament, toward the circumferential wall of the bone tunnel so as to secure the graft ligament to the circumferential wall.

2. The system of claim 1, wherein the at least two concavities includes a first concavity on said first side of the graft ligament fixing element and a second concavity on said second side of the graft ligament fixing element that is opposed to the first side of the graft ligament fixing element.

3. The system of claim 2, wherein movement of the locking element urges the first side and the second side of the graft ligament fixing element apart.

4. The system of claim 2, wherein the graft ligament fixing element comprises a sleeve and the locking element is configured for movement within the sleeve.

5. The system of claim 2, wherein the graft ligament fixing element comprises a sleeve and includes a frangible portion so that as the first and second sides are urged towards the circumferential wall, a split forms in the sleeve at the frangible portion.

6. The system of claim 1, wherein the locking element is selected from the group consisting of a rocker arm, an expansion plug, a threaded expansion plug, and a transverse screw.

7. A method for attaching a graft ligament to a bone, the method comprising:
providing an opening in the bone, the opening having a circumferential wall;
inserting the graft ligament and a graft ligament fixing element in the opening, the graft ligament fixing element having a plurality of side wall portions configured to contact a graft ligament portion when the graft ligament is placed in the bone tunnel, the side wall portions including at least two concavities extending longitudinally, distinct portions of the graft ligament being nested within the concavities between each concavity and the bone tunnel;
inserting a locking element in the opening to engage at least a portion of the graft ligament fixing element, the locking element being separated from the graft ligament by the graft ligament fixing element;
wherein a first side and a second side of the side wall portions are deformable and movement of the locking element causes a change in shape in the first side and the second side; and
moving the locking element to cause at least a portion thereof to engage the graft ligament fixing element to urge the sidewall portions, and hence the graft ligament, toward the circumferential wall of the opening to secure the graft ligament to the circumferential wall.

8. The system of claim 1, wherein the at least two concavities includes a first concavity on said first side of the graft ligament fixing element and a second concavity on said second side of the graft ligament fixing element that is opposed to the first side of the graft ligament fixing element.

9. The method of claim 8, wherein movement of the locking element includes urging the first side and the second side of the graft ligament fixing element apart.

10. The method of claim 8, wherein the graft ligament fixing element comprises a sleeve and the locking element is moved within the sleeve.

11. The method of claim 8, wherein the graft ligament fixing element comprises a sleeve and includes a frangible portion so that urging the first and second sides towards the circumferential wall includes forming a split in the sleeve at the frangible portion.

12. The method of claim 7, wherein the locking element is selected from the group consisting of a rocker arm, an expansion plug, a threaded expansion plug, and a transverse screw.

* * * * *